United States Patent [19]

Logan et al.

[11] Patent Number: 5,192,755
[45] Date of Patent: Mar. 9, 1993

[54] PREGNANE DERIVATIVES AS IMMUNOMODULATORS

[75] Inventors: Robert T. Logan, Lanark, Scotland; Gilbert F. Woods, Beaumaris, Wales

[73] Assignee: Akzo N.V., Arnhem, Netherlands

[21] Appl. No.: 525,299

[22] Filed: May 17, 1990

Related U.S. Application Data

[63] Continuation of Ser. No. 3,107, Jan. 14, 1987, abandoned.

[30] Foreign Application Priority Data

Jan. 15, 1986 [GB] United Kingdom ............... 8600879

[51] Int. Cl.$^5$ .............................................. A61K 31/56
[52] U.S. Cl. ..................................... 514/180; 514/177; 514/885
[58] Field of Search ............... 552/588; 514/177, 180, 514/885

[56] References Cited

U.S. PATENT DOCUMENTS

| | | | |
|---|---|---|---|
| 3,162,630 | 12/1964 | Morand | 260/239.55 |
| 3,483,236 | 12/1969 | Schaub | 260/397.45 |
| 3,520,908 | 7/1970 | Hewett et al. | 260/397.45 |
| 3,531,503 | 9/1970 | Cereghetti et al. | 260/397.45 |
| 4,678,609 | 7/1987 | Engels | 260/397.45 |
| 4,839,282 | 6/1989 | Weber et al. | 435/61 |

OTHER PUBLICATIONS

*Steroid Reactions* (1963), p. 202; Djerassi.
Chemical Abstracts, Abstract No. 47795p, vol. 78, p. 278 (Feb. 1973).
Max Samter, M.D., Editor, *Immunological Diseases*, "86. Pharmacological Immunosuppression", vol. II, pp. 1522-1533 (1978).

*Primary Examiner*—Frederick E. Waddell
*Assistant Examiner*—Kimberly R. Jordon
*Attorney, Agent, or Firm*—Spencer, Frank & Schneider

[57] ABSTRACT

The invention provides novel pregnane derivatives having the formula:

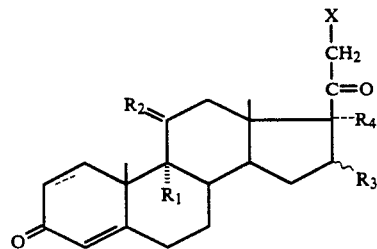

wherein X=F, Cl or Br; $R_1$=F or Cl; $R_2$=H($\beta$OH) or O; $R_3$=alkyl(1-4 C); $R_4$=alkyl(1-4 C); and the dotted line indicates the optional presence of a double bond.

The novel compounds have been found to possess immunomodulating properties.

24 Claims, No Drawings

PREGNANE DERIVATIVES AS IMMUNOMODULATORS

This application is a continuation of application Ser. No. 07/003,107, filed Jan. 14, 1987, now abandoned.

The present invention relates to novel pregnane derivatives substituted in 21-position by F, Cl or Br, to processes for their preparation and to pharmaceutical compositions containing one or more of said derivatives as active constituent.

More particularly, the invention relates to novel pregnane derivatives of the formula:

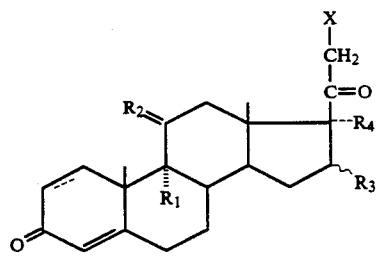

wherein
X=F, Cl or Br, preferably Cl:
$R_1$=F or Cl, preferably F;
$R_2$=H($\delta$OH) or O, preferably H($\delta$OH);
$R_3$=alkyl (1–4 C), preferably $CH_3$ which is preferably a $\alpha$-position;
$R_4$=alkyl(1–4 C), preferably $CH_3$; and the dotted line indicates the optional presence of a double bond in 1,2-position, said double bond preferably being present.

The compounds of the present invention possess very interesting immunomodulating properties. They exhibit a higher affinity for the corticosteroid leucocyte receptors and have reduced hormonal (glucocorticoid) effects compared with known glucocorticoids such as dexamethasone. In vitro and in vivo tests have shown that the novel compounds of the present invention, particularly the 21-chloro compounds, stimulate the humoral immune response over a wide range of relatively low doses and suppress the cell mediated immune response at relatively high doses. At low doses the novel compounds cause a functionel maturation of the immune system in response to antigen stimulation.

The compounds according to the invention are therefore useful for treating a wide range of diseases involving a disorder of the immune system, e.g. cancer, auto-immune diseases, and also for preventing the rejection of transplants.

The compounds within the purview of this invention can be prepared by methods obvious to those skilled in the art. They may be prepared e.g. by starting from the corresponding 21-hydroxy steroid and converting the 21-hydroxy group into the 21-sulphonate thereof e.g. into the 21-mesylate or the 21-tosylate, after which the 21-sulphonate is reacted with an alkalimetal halide, e.g. lithium chloride or potassium fluoride, to obtain the desired 21-halo steroid.

The conversion of the 21-hydroxy steroid into the 21-sulphonate is carried out by reaction with the appropriate sulphonic acid halide, such as methanesulphonyl chloride or toluenesulphonyl chloride, at low temperature (0°–20° C.) in the presence of a base, preferably an organic base such as pyridine, that can also serve as the solvent. The reaction of the 21-sulphonate with the alkalimetal halide is carried out in a suitable solvent, such as dimethylformamide, dimethylacetamide or ethyleneglycol, at elevated temperature, conveniently under reflux.

It is also possible to convert the 21-hydroxy steroid into the 21-halo steroid directly by reacting the 21-hydroxy steroid with a sulphonyl halide, such as methanesulphonyl chloride, in dimethylformamide at elevated temperature, i.e. in the range of 50° to 70° C.

Another method for preparing the compounds according to the invention is to start from the corresponding $\Delta^{9(11)}$ compound and introducing into 9,11-position the required substituents by methods known in the art, such as converting the $\Delta^{9(11)}$ double bond into the 9$\alpha$-bromo-11$\beta$-hydroxy compound or an 11$\beta$-ester thereof, e.g. by reaction with N-bromo-succinimide in dimethylformamide in the presence of perchloric acid, and transforming the 9$\alpha$-bromo-11$\beta$-hydroxy compound or the 11$\beta$-ester thereof under basic conditions into the corresponding 9$\beta$11$\beta$-epoxide, which is subsequently opened with a halogen acid to give the desired 9$\alpha$-halo-11$\beta$-hydroxy derivative. Reacting a $\Delta^{9(11)}$ compound with N-chloro-succinimide gives directly the 9$\alpha$-chloro-11$\beta$-hydroxy compound.

Starting materials for the above reactions are described in literature, e.g. in U.S. Pat. No. 3,520,908 or can readily be prepared from the 16$\alpha$, 17$\alpha$-dialkyl compounds described in said U.S. Specification, e.g. 21-hydroxy-$\Delta^{9(11)}$ compounds can be converted into the corresponding 21-halo-$\Delta^{9(11)}$ compounds by the method described herinbefore or 11,21-dihydroxy compounds can be converted into the corresponding 21-halo-$\Delta^{9(11)}$ compounds in a one-step synthesis using an organic sulphonylchloride, such as methane sulphonylchloride, in pyridine.

The compounds according to the invention can also be prepared starting from the corresponding 21-iodo compound (see e.g. U.K. Patent Specification 1 458 517) and reacting this compound with an alkalimetal chloride bromide, or fluoride in a suitable solvent such as N-methyl-pyrrolidone.

In compounds according to the invention containing a $\Delta^4$3-oxo group an additional double bond in position $C_1$-$C_2$ may be introduced by known chemical means such as by reaction with a suitable quinone derivative, e.g. dichlorodicyanobenzoquinone, or with seleniumdioxide or a derivative thereof such as diphenyldiseleninic anhydride.

A double bond in position $C_1$-$C_2$ may also be introduced microbiologically by incubation with a 1,2-dehydrogenating micro-organism, for example *Corynebacterium simplex, Bacillus spaericus* or *Bacillus subtillis.*

A $\Delta^{1,4}$-3-oxo coumpound can be converted into a $\Delta^4$-3-oxo compound by $\Delta^1$-hydrogenation, e.g. by catalytic hydrogenation in the presence of the homogenous catalyst tris-triphenylphosphine rhodium (I) chloride.

An 11-hydroxy group may, if required, be oxidised to an 11-keto group, e.g. with chromic acid.

If an intermediate contains already an 11-hydroxy group, but not yet the 9$\alpha$-fluoro or -chloro group, such intermediate is dehydrated in 9,11-position and the $\Delta^{9(11)}$ compound thus obtained is converted into a 9$\alpha$-halo-11$\beta$-hydroxy compound by the method described hereinbefore.

The compounds of the present invention can be administered enterally or parenterally in the usual administration forms, i.e. pharmaceutical compositions, for which purpose they are mixed with one or more pharmaceutically acceptable non-toxic carriers and/or the usual excipients. The pharmaceutical compositions include tablets, pills, coated tablets and suppositories for enteral administration and solutions, suspensions and emulsions for parenteral administration (injection).

Other methods of administration include sublingual administration, nasal sprays, inhalation and topical administration in the form of ointments, creams, lotions or sprays.

The invention is further illustrated by the following Examples.

EXAMPLE I a) 9α-Fluoro-11β,21-dihydroxy-16 α,17α-dimethylpregna-1,4-diene-3,20-dione 21-methanesulphonate To a stirred suspension of 9α-fluoro-11β,21-dihydroxy-16α,17α-dimethylpregna-1,4-diene-3,20-dione (2.5 g) in pyridine (12.51 ml) was added methane-sulphonyl chloride (1.25 ml) while the temperature was maintained between 2° C. and 10° C. The mixture was stirred for a further 30 min. at below 10° C. Water (50 ml) was added and while stirring was continued, the precipitated gum solidified. The solid was filtered off, washed with water and dried in vacuo. Recrystallisation from acetone-ether gave the title methanesulphonate (2.77 g), m.p. 229°–231° C. (dec), $[\alpha]_D^{20}$ (pyridine) +102°.

b) 21-Chloro-9α-fluoro-11β-hydroxy-16α,17α-dimethyl-pregna-1,4,-diene-3,20-dione Lithium chloride (1.5 g) was added to a solution of 9α-fluoro-11β,21-dihydroxy-16α,17α-dimethylpregna-1,4-diene-3,30-dione 21-methane-sulphonate (3 g) in dimethylformamide (30 ml) and the mixture was heated under reflux for 20 min. After cooling, the mixture was poured into water and the precipitated solid was filtered off, washed with water and dried in vacuo. Chromatography on silica and recrystallisation of the mid-fractions eluted from methylene chloride-ether (1:1) gave the title chlorosteroid (1.75 g), m.p. 252°–254° C.; $]\alpha]_D^{20}$ (CHCl$_3$) +64°.

EXAMPLE II

21-Chloro-9α-fluoro-16α,17α-dimethyl-pregna-1,4-diene-3,11,20-trione

Jones reagent (2.07M; 2.9 ml) was added dropwise to a solution of 21-chloro-9α-fluoro-11β-hydroxy-16α,17α-dimethyl-pregna-1,4-diene-3,20-dione (960 mg) in acetone (25 ml) at 0° C. The reaction mixture was poured into water at 0° C. The precipitated solid was filtered off and dissolved in methylene chloride. The solution was washed with sodium carbonate at 0° C. and then with water and dried over sodium sulphate. Removal of the solvent under reduced pressure gave a solid (954 mg) which recrystallized from acetone to give the title compound (840 mg) as colourless needles, m.p. 238°–240° C.

EXAMPLE III

9α,21-Difluoro-11β-hydroxy-16α,17α-dimethyl-pregna-1,4-diene-3,20-dione

Anhydrous potassium fluoride (4.16 g) was added to a suspension of 9α-fluoro-11β,21-dihydroxy-16α,17α-dimethylpregna-1,4-diene-3,20-dione 21-methanesulphonate (2.08 g) in ethyleneglycol (45 ml) and the mixture heated under nitrogen for 1 h. at 165° C. The mixture was poured into water at 0° C. and the precipitated solid was filtered off. Chromatography and recrystallization from chloroform-methanol afforded the title compound, m.p. 324°–326° C. (decomp.).

EXAMPLE IV

9α,21-Difluoro-16α,17α-dimethylpregna-1,4-diene-3,11,20-trione

Jones reagent (2.7M) was added to a stirred suspension of 9α,21-difluoro-11β-hydroxy-16α,17α-dimethylpregna-1,4-diene-3,20-dione (400 mg) until oxidation of the 11-hydroxy function was complete. The mixture was poured into water at 0° C., and the precipitated solid was filtered off and dissolved in methylene chloride. The solution was dried over sodium sulphate and the solvent removed in vacuo. Recrystallisation from ether gave the title compound, m.p. 223°–224° C.

EXAMPLE V

In a similar way as described in Example I or III the following compounds were prepared starting from the corresponding 21-hydroxy compounds:

21-chloro-9α-fluoro-11β-hydroxy-16α,17α-dimethyl-pregna-4-ene-3,20-dione;
21-chloro-16α-ethyl-9α-fluoro-11β-hydroxy-17α-methyl-pregna-1,4-diene-3,20-dione;
21-chloro-17α-ethyl-9α-fluoro-11β-hydroxy-16α-methyl-pregna-4-ene-3,20-dione;
16α-ethyl-9α,21-difluoro-11β-hydroxy-17α-methyl-pregna-1,4-diene-3,20-dione;
21-bromo-16α-ethyl-9α-fluoro-11β-hydroxy-17α-methyl-pregna-4-ene-3,20-dione;
21-bromo-9α-fluoro-11β-hydroxy-16α,17α-dimethyl-pregna-1,4-diene-3,20-dione;
9α,21-dichloro-11β-hydroxy-16α,17α-dimethyl-pregna-1,4-diene-3,20-dione;

which are then converted into the corresponding 11-ketones in a similar way as described in Example II or IV.

EXAMPLE VI

21-Chloro-9α-fluoro-11β-hydroxy-16α,17α-dimethyl-pregna-1,4-diene-3,20-dione Methanesulphonyl chloride (0.5 ml) was added to a solution of 11β,21-dihydroxy,-9α-fluoro-16α,17α-dimethyl-pregna-1,4-diene-3,20-dione in dimethylformamide (20 ml) and the mixture was heated at 60° C. for 1 hour. Then a second amount of methanesulphonyl chloride (0.5 ml) was added and the mixture was heated at 60° C. for 3 hours, then poured into water at 0° C. the precipitate filtered off, washed and recrystallized from acetone-ether to give the title compound (0.5 g), m.p. 251°–254° C.

EXAMPLE VII

21-Chloro-9α-fluoro-11β-hydroxy-16α,17α-dimethyl-pregna-1,4-diene-3,20-dione Lithium chloride (1.26 g) was added to a solution of 9α-fluoro-11β-hydroxy-21-iodo-16α,17α-dimethyl-pregna-1,4-diene-3,20-dione (9.5 g) in N-methyl-2-pyrrolidinone (190 ml) and the stirred mixture was heated at 55° C. for 1 h in an atmosphere of nitrogen. The mixture was cooled and then poured into water at 0° C. The precipitated solid was filtered off, washed with water and dissolved in methylene chloride. The solution was washed with water, dried over sodium sulphate and the solvent was removed under reduced pressure. The resultant colourless solid (7.8 g) was recrystallised from methylene chloride-ether to give 21-chloro-9α-fluoro-11β-hydroxy-16α,17α-dimethyl-pregna-1,4-diene-3,20-dione (5–6 g), m.p. 252°–254° C.; $[\alpha]_D^{20}$ (CHCl$_3$) +64° C.

EXAMPLE VIII a)
21-Chloro-11β-hydroxy-16α,17α-dimethylpregna-1,4-diene-3,20-dione

Lithium chloride (1.26 g) was added to a solution of 21-iodo-11β-hydroxy-16α,17α-dimethylpregna-1,4-diene-3,20-dione (9.5 g) in N-methyl-2-pyrrolidinone (190 ml) and the stirred mixture was heated at 55° C. for 1 h in an atmosphere of nitrogen. The mixture was cooled and then poured into water at 0° C. The precipitated solid was filtered off, washed with water and dissolved in methylene chloride. The solution was washed with water, dried over sodium sulphate and the solvent was removed under reduced pressure. The resultant colourless solid (7.8 g) was recrystallised from methylene chloride ether to give 21-chloro-11α-hydroxy-16α,17α-dimethylpregna-1,4-diene-3,20-dione (5–6 g), m.p. 260°–265° C.; $[\alpha]_D^{20}$ (CHCl$_3$) +63.920 .

b)
21-Chloro-16α,17α-dimethylpregna-1,4,9(11)-triene-3,20-dione

To a stirred mixture of 21-chloro-11β-hydroxy-16α, 17α,-dimethylpregna-1,4-diene-3,20-dione (7.8 g) in dimethylformamide (78 ml) and collidine (23 ml) at 10° C. was added dropwise over 3–4 min a solution (3.9 ml) of methanesulphonyl chloride containing sulphur dioxide (5%). The mixture was then stirred for 1.75 h at ambient temperature and sulphuric acid (5N; 700 ml) at 0° C. was added. The precipitated solid was filtered off, washed with water and then dissolved in methylene chloride. The solution was washed with water until free of acid and dried over sodium sulphate. Removal of the solvent under reduced pressure gave a solid (6.7 g ) which was dissolved in toluene and chromatographed on a column of silica. The fractions eluted with toluene-ethyl acetate (19:1) were evaporated to dryness to give a solid which was recrystallised from acetone-hexane to give 21-chloro-16α,17α,-dimethylpregna-1,4,9(11)-triene-3,20-dion (4.6 g), m.p. 160°–162° C;$[a]_D^{20}$ (CHCl$_3$) −1.9°.

9α-Bromo-21-chloro-11β-hydroxy-16α,17α-dimethyl-pregna-1,4-diene-3,20-dione 11-formate A stirred solution of 21-chloro-16α,17α-dimethyl-pregna-1,4,9(11)-triene-3,20-dione (78 g) in dimethylformamide (816 ml) was treated dropwise at 5° C. with perchloric acid (70%; 19.6 ml) keeping the temperature below 10° C. N-Bromosuccinimide (57.2 g) was added over 10 min and the mixture was stirred for a further 1.25 h at 8°–10° C. Sodium bisulphite (7 g) in water (40 ml) was added and the mixture was poured into water (8 l) at 0° C. The precipitated solid was filtered off, and dissolved in methylene chloride. The solution was washed with water, dried over sodium sulphate and the solvent was removed under reduced pressure to give 9α-bromo-21-chloro-11β-hydroxy-16α,17α-dimethyl-pregna-1,4-diene-3,20-dione 11-formate (99.6 g).

d)
21-Chloro-16α,17α-dimethyl-9β,11β-oxidopregna-1,4-diene-3,20dione

To a stirred solution of 9α-bromo-21-chloro-11β-hydroxy-16α,17α-dimethylpregna-1,4-diene-3,20-dione 11-formate (99 g) in tetrahydrofuran (990 ml) at 6° C. was added a solution of sodium methoxide (12.95 g) in methanol (990 ml). The mixture was stirred at 6°–10° C. for 2 h and the solution was then adjusted to pH6 with acetic acid. The mixture was concentrated to one half of the volume and then poured into water (4 l) at 0° C. Isolation of the product through ether and then methylene chloride gave a yellow solid (68.4 g) Two recrystallisations from methylene chloride-ether gave 21-chloro-16α,17α-dimethyl-9β,11β-oxidopregna-1,4-diene-3,20-dione (657 mg), m.p. 201°–202° C.; $[\alpha]_D^{20}$ (CHCl$_3$) +18.6°.

e)
21-Chloro-9α-fluoro-11β-hydroxy-16α,17α-dimethyl-pregna-1,4-diene-3,20 dione To a stirred suspension of 21-chloro-16 α,17α, dimethyl-98.11β-oxidopregna-1,4-diene-3,2--dione (1.0 g) in diglyme (9.5 ml) at 0° C. was added a solution of hydrogen fluoride in diglyme (12M; 0.63 ml) cooled at 0° C., immediately followed by boron trifluoride etherate in ether (45% BF$_3$; 0.95 ml) cooled at 0° C. The mixture was stirred for a further 2 h at ambient temperature and then poured into water (50 ml) containing sodium acetate (2.84 g). The precipitated solid was filtered off, washed with water and dissolved in methylene chloride. The solution was washed with water, dried over sodium sulphate and the solvent was removed under reduced pressure to give a solid (1.1 g). Recrystallisation from methylene chloride-ether gave 21-chloro-9α-fluoor-11β-hydroxy-16α, 17α-dimethyl-pregna-1,4-diene-3,20-dione (708 mg), m.p. 252°–254° C; $[\alpha]_D^{20}$ (CHCl$_3$) 30Γ°.

EXAMPLE IX

9α,21-Dichloro-11β-hydroxy-16α,17α-dimethylpregna-1,4-diene-3,20 dione

To a mixture of 21-chloro-16α,17α-dimethylpregna-1,4,9(11)-triene-3,20-dione (0.5 g), dioxan (9.5 ml) and water (0.7 ml) at 20° C. was added portionwise N-chloro-succinimide (0.5 g) and then a solution of perchloric acid (70%; 0.05 ml) in water (0.08 ml). The mixture was stirred at room temperature for 70 h. A solution of sodium acetate (200 mg) and sodium bisulphite (125 mg) in water (1.5 ml) was added and the mixture was poured into water (100 ml) at 0° C. The precipitated solid was filtered off and dissolved in methylene chloride. The solution was washed with water, dried over sodium sulphate and the solvent was removed under reduced pressure. Trituration with ether and recrystallisation from acetone afforded 9α,21-dichloro-11β-hydroxy-16α,17α-dimethylpregna-1,4-diene-3,20-dione, m.p. 235°–241° C. (decomp.).

EXAMPLE X

21-Bromo-9α-fluoro-11β-hydroxy-16α,17α-dimethyl-pregna-1,4-diene-3,20-dione

A stirred suspension of 9α-fluoro-11β,21-dihydroxy-16α,17α-dimethylpregna-1,4-diene-3,20-dione 21-methanesulphonate (454 mg) and sodium bromide (1.14 g) in acetone (21.4 ml) was heated under reflux for 28 h and the mixture was then poured into water (200 ml). The precipitated solid was filtered off, washed with water and then dried under reduced pressure at 70° C. The resultant colourless solid was dissolved in methylene chloride and chromatographed on a column of silica. The fractions eluted with ether through to methylene chloride-ether (1:1) gave a white solid (380 mg) which was recrystallised from methylene chloride-ether to give 21-bromo-9α-fluoro-11β-hydroxy-16α,17α-dimethylpregna-1,4-diene 3,20-dione (290 mg), m.p. 195°-200° C. (decomp.); $[\alpha]_D^{20}$ 30 71.0°(CHCl$_3$).

EXAMPLE XI a) 21-Chloro-16α,17α-dimethylpregna-1,4,9(11)-triene-3,20-dione

A solution of 21-hydroxy-16α,17α-dimethylpregna-1,4,9(11)-triene-3,20-dione (200 mg), methanesulphonyl chloride (0.1 ml) and dimethylformamide (2 ml) was heated at 60° C. for 1.5 h and the mixture was then poured into water (25 ml). The precipitated solid was filtered off and dissolved in methylene chloride. The solution was washed with water, dried over sodium sulphate and the solvent was removed under reduced pressure. The resultant gum (240 mg) was crystallised from acetone-petroleum ether (60-80) to give 21-chloro-16α,17α-dimethylpregna-1,4,9(11)-triene-3,20-dione (135 mg), m.p. 160°-162° C.; $[\alpha]_D^{20}$ (CHCl$_3$) −1.9°.

b) 21-Chloro-9α-fluoro-11β-hydroxy-16α,17α-dimethylpregna-1,4-diene-3,20-dione

In a similar way as described in Example VIII, c)-e), the product of Example XI a) was converted into the title compound, m.p. 252°-254° C.; $[\alpha]_D^{20}$ (CHCl$_3$) +64°.

We claim:

1. A method of supporting the cellular immune system comprising administering a pharmaceutical composition having the formula:

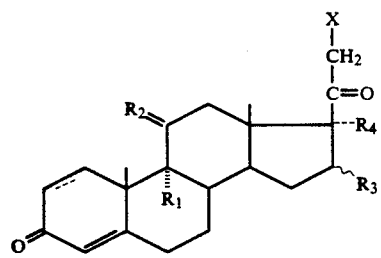

wherein
X=F, Cl or Br;
R$_1$=F or Cl;
R$_2$=H(βOH) or O;
R$_3$=alkyl (1-4 C);
R$_4$=alkyl (1-4 C); and
the dotted line indicates the presence of a single or a double bond in 1,2-position,
and a pharmaceutically acceptable non-toxic carrier, in an effective amount to suppress the cellular immune system.

2. The method of suppressing the cellular immune system set forth in claim 1, wherein X=Cl.

3. The method of suppressing the cellular immune system set forth in claim 1, wherein R$_1$=F.

4. The method of suppressing the cellular immune system set forth in claim 1, wherein R$_2$=H(62 OH).

5. The method of suppressing the cellular immune system set forth in claim 1, wherein R$_3$=CH$_3$.

6. The method of suppressing the cellular immune system set forth in claim 1, wherein R$_3$=α-CH$_3$.

7. The method of suppressing the cellular immune system set forth in claim 1, wherein R$_4$=CH$_3$.

8. The method of suppressing the cellular immune system set forth in claim 1, including a double bond in the 1,2-position.

9. A method of mitigating the rejection of a transplant comprising administering a pharmaceutical composition having the formula

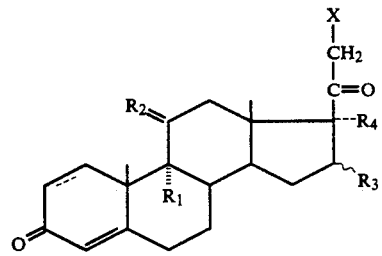

wherein
X=F, Cl or Br;
R$_1$=F or Cl;
R$_2$=H(βOH) or O;
R$_3$=alkyl(1-4 C);
R$_4$=alkyl(1-4 C)l and
the dotted line indicates the presence of a single or a double bond in the 1,2-position.
and a pharmaceutically acceptable non-toxic carrier, in an effective amount to mitigate rejection of a transplant.

10. The method of mitigating the recjection of a transplant set forth in claim 9, wherein X=Cl.

11. The method of mitigating the rejction of a transplant set forth in claim 9, wherein R$_1$=F.

12. The method of mitigating the rejcetion of a transplant set forth in claim 9, wherein R$_2$=H(βOH).

13. The method of mitigating the rejection of a transplant set forth in claim 9, wherein R$_3$=CH$_3$.

14. The method of mitigating the rejection of a transplant set forth in claim 9, wherein R$_3$=α-CH$_3$.

15. The method of mitigating the rejection of a transplant set forth in claim 9, wherein R$_4$=CH$_3$.

16. The method of mitigating the rejection of a transplant set forth in claim 9, including a double bond in the 1,2-position.

17. A method of stimulating the humoral immune system comprising administering a pharmaceutical composition having the formula:

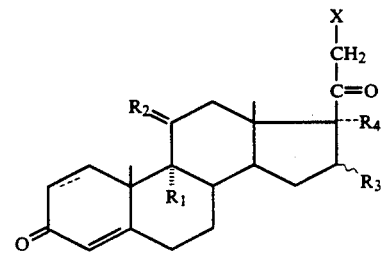

wherein
- X = F, Cl or Br;
- $R_1$ = F or Cl;
- $R_2$ = H($\beta$OH) or O;
- $R_3$ = alkyl(1-4 C);
- $R_4$ = alkyl(1-4 C); and
- the dotted line indicates the presence of a single or a double bond in the 1,2-position, and a pharmaceutically acceptable non-toxic carrier, in an effective amount to stimulate the humoral immune system.

18. The method of stimulating the humoral immune system set forth in claim 17, wherein X = Cl.

19. The method of stimulating the humoral immune system set forth in claim 17, wherein $R_1$ = F.

20. The method of stimulating the humoral immune system set forth in claim 17, wherein $R_2$ = H($\beta$OH).

21. The method of stimulating the humoral immune system set forth in claim 17, wherein $R_3$ = $CH_3$.

22. The method of stimulating the humoral immune system set forth in claim 17, wherein $R_3$ = $\alpha$-$CH_3$.

23. The method of stimulating the humoral immune system set forth in claim 17, wherein $R_4$ = $CH_3$.

24. The method of stimulating the humoral immune system set forth in claim 17, including the double bond in the 1,2-position.

* * * * *